United States Patent [19]
Braish et al.

[11] Patent Number: 5,939,550
[45] Date of Patent: Aug. 17, 1999

[54] PROCESS FOR PREPARING DERIVATIVES OF AZABICYCLO NAPHTHYRIDINE CARBOXYLIC ACID COMPRISING A DIPEPTIDE

[75] Inventors: Tamim F. Braish, Ledyard; Michael J. Castaldi, Pawcatuk; Harry A. Watson, Jr., Groton, all of Conn.

[73] Assignee: Pfizer Inc., New York, N.Y.

[21] Appl. No.: 08/981,350

[22] PCT Filed: Mar. 27, 1996

[86] PCT No.: PCT/IB96/00257

§ 371 Date: Mar. 11, 1998

§ 102(e) Date: Mar. 11, 1998

[87] PCT Pub. No.: WO97/00268

PCT Pub. Date: Jan. 3, 1997

Related U.S. Application Data

[63] Continuation of application No. 08/490,827, Jun. 15, 1995, abandoned.

[51] Int. Cl.$^6$ .................................................. C07D 471/04
[52] U.S. Cl. ............................................................ 546/123
[58] Field of Search ................................................ 546/123

[56] References Cited

U.S. PATENT DOCUMENTS

| | | | |
|---|---|---|---|
| 4,851,418 | 7/1989 | Sanchez | 514/300 |
| 5,164,402 | 11/1992 | Brighty | 514/300 |

FOREIGN PATENT DOCUMENTS

| | | |
|---|---|---|
| 0413455 | 2/1991 | European Pat. Off. . |

OTHER PUBLICATIONS

Chemical Abstracts, vol. 111, No. 17, Abstract No. 153779 w (1989).

*Primary Examiner*—Bernard Dentz
*Attorney, Agent, or Firm*—Peter C. Richardson; Paul H. Ginsburg

[57] ABSTRACT

A multi-step process for preparing a dipeptide derivative of 7-(6-amino-3-azabicyclo[3.1.0.]hex-3-yl)-6-fluoro-1-(2,4-difluorophenyl)-1,4-dihydro-4-oxo-1,8-naphthyridine-3-carboxylic acid, in the form of a pharmaceutically acceptable acid addition salt is disclosed.

21 Claims, No Drawings

PROCESS FOR PREPARING DERIVATIVES OF AZABICYCLO NAPHTHYRIDINE CARBOXYLIC ACID COMPRISING A DIPEPTIDE

This application is a 371 of PCT/IB96/00257 filed Mar. 27, 1996, which is a continuation of Ser. No. 08/490,827 filed Jun. 15, 1995, now abandoned.

This invention relates to a new and useful process for preparing a naphthyridine carboxylic acid. More particularly, it is concerned with a novel method for preparing 7-[(1α,6α,7α)-6-(L-Ala-L-Ala-amino)-3-azabicyclo [3.1.0]hex-3-yl]-6-fluoro-1-(2,4-difluorophenyl)-1,4-dihydro-4-oxo-1,8-naphthyridine-3-carboxylic acid as a pharmaceutically acceptable acid addition salt. It is especially concerned with the preparation of the corresponding methanesulfonic acid salt of the aforementioned naphthyridine carboxylic acid, which serves as a water-soluble prodrug of the known antibacterial agent 7-[(1α,5α,6α)-6-amino-3-azabicyclo[3.1.0]-hex-3-yl]-6-fluoro-1-(2,4-difluorophenyl)-1,4-dihydro-4-oxo-1-naphthyridine-3-carboxylic acid.

In accordance with the prior art, there is described in U.S. Pat. No. 5,164,402 to K. E. Brighty a method for preparing 7-[(1α,5α,6α)-6-(L-Ala-L-Ala-amino)-3-azabicyclo[3.1.0] hex-3-yl-6-fluoro-1-(2,4-difluorophenyl)-1,4-dihydro-4-oxo-1,8-naphthyridine-3-carboxylic acid (prodrug acid) by first reacting 7-[(1α,5α,6α)-6-amino-3-azabicyclo[3.1.0] hex-3-yl)-6-fluoro-1-(2,4-difluorophenyl)-1,4-dihydro-4-oxo-1,8-naphthyridine-3-carboxylic acid with N-tert.-butoxycarbonyl-L-alanine, to eventually yield the intermediate mono-L-Ala-amino prodrug, followed by an additional reaction of the latter product with still further N-tert.-butoxycarbonyl-L-alanine to ultimately yield the desired prodrug final product. The same patent reference also describes the conversion of 7-[(1α,5α,6α)-6-amino-3-azabicyclo[3.1.0]hex-3-yl]-6-fluoro-1-(2,4-difluorophenyl)-1,4-dihydro-4-oxo-1,8-naphthyridine-3-carboxylic acid to 7-[(1α,5α,6α)-6-(L-Ala-L-Leu-amino)-3-azabicyclo[3.1.0] hex-3-yl]-6-fluoro-1-(2,4-difluorophenyl)-1,4-dihydro-4-oxo-1,8-naphthyridine-3-carboxylic acid by first reacting the aforesaid N-deprotected drug acid starting material with N-benzyloxycarbonyl-L-alanyl-L-leucine to eventually give the corresponding prodrug acid compound having two different amino acids in the side chain at the 6-position of the molecule. In each instance, the N-deprotected drug acid is obtained from the corresponding N-protected drug ethyl ester by means of acid hydrolysis with hot concentrated hydrochloric acid at reflux temperatures, while the prodrug acid final product obtained in the last step is also achieved in essentially the same manner, but under somewhat milder reactions conditions. In the aforesaid process, it is possible for the unprotected carboxy group of 7-[(1α,5α,6α)]-6-amino-3-azabicycl[3.1.0]hex-3-yl]-6-fluoro-1-(2,4-difluoro-phenyl)-1,4-dihydro-4-oxo-1,8 -naphthyridine-3-carboxylic acid to engage in a number of side reactions of the self-condensation type, thereby leading to somewhat diminished yields of the desired prodrug acid final product of the present invention.

BACKGROUND ART

In accordance with the present invention, there is now provided a new and improved process for preparing the prodrug herein before discussed above, viz., 7-[(1α,5α,6α)-6-(L-Ala-L-Ala-amino)-3-azabicyclo[3.1.0]hex-3-yl-6-fluoro-1-(2,4-difluorophenyl)-1,4-dihydro-4-oxo-1,8-naphthyridine-3-carboxylic acid as a pharmaceutically acceptable acid addition salt, in pure form and in high yield by a novel three-step method, starting from the appropriate N-protected drug ester that is typically an N-protected 7-[(1α,5α,6α)-6-amino-3-azabicyclo[3.1.0]hex-3-yl]-fluoro-1-(2,4-difluorophenyl)-1,4-dihydro-4-oxo-1,8-naphthyridine-3-carboxylic acid lower alkyl ($C_1$–$C_4$) ester and proceeding through the following sequence of reactions, as outlined in the accompanying reaction scheme.

REACTION SCHEME

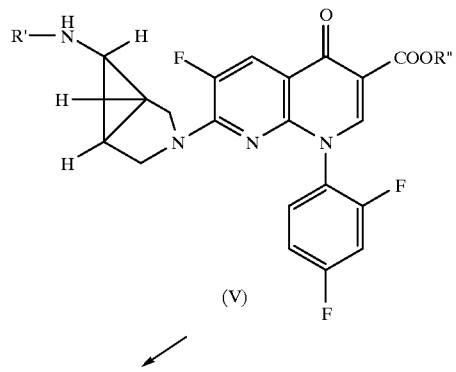

(V)

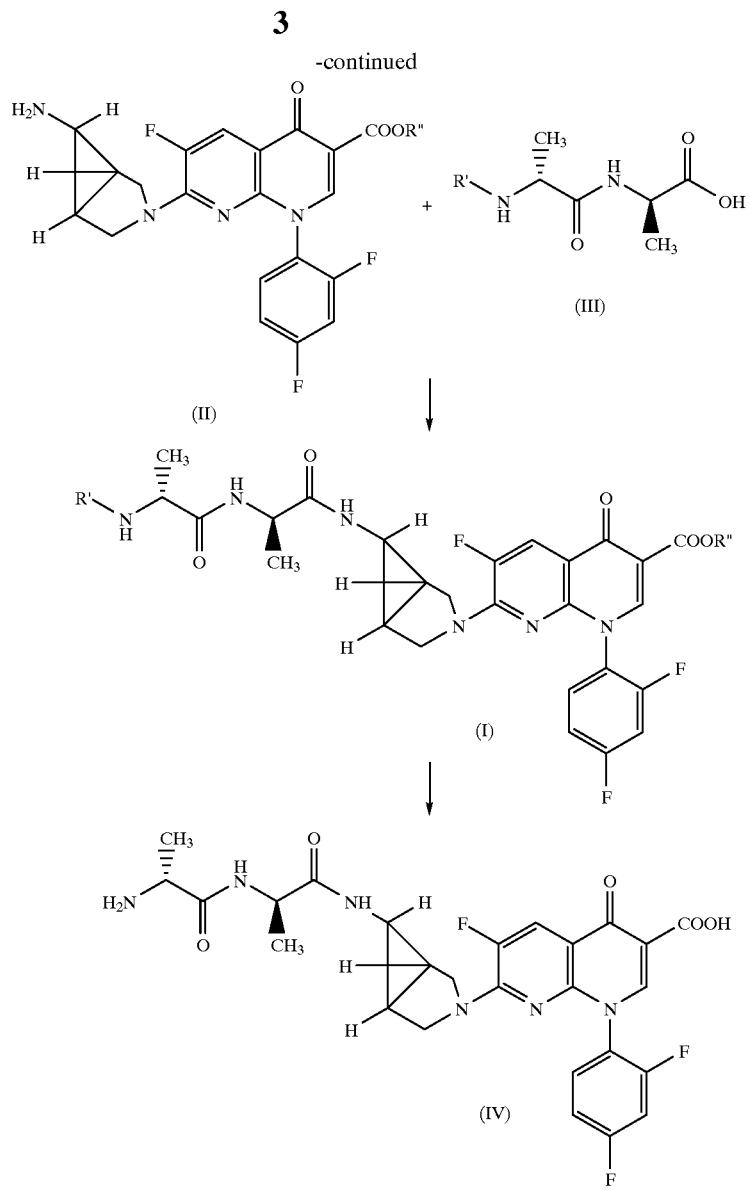

More particularly, the overall process of the invention involves the steps of:

(a) treating an N-protected 7-[(1α,5α,6α)-6-amino-3-azabicyclo[3.1.0]hex-3-yl]-6-fluoro-1-(2,4-difluorophenyl)-1,4-dihydro-4-oxo-1,8-naphthyridine-3-carboxylic acid $C_1$–$C_4$ alkyl ester [see formula (V)], wherein R' is an N-protecting group like benzyloxycarbonyl, $C_1$–$C_4$ alkoxycarbonyl or $C_1$–$C_4$ alkanoyl and R" is an alkyl group having from one to four carbon atoms, with a strongly-protic acid to selectively remove the N-protecting group;

(b) then condensing the resulting amino ester compound [see formula (II)] with an N-protected L-alanyl-L-alanine dipeptide compound [having formula (III)] in the presence of dehydrating agent to form the corresponding N-protected prodrug ester as the desired condensation product; and (c) thereafter hydrolyzing the intermediate N-protected prodrug ester [see formula (I)] in the presence of a pharmaceutically-acceptable strong acid to convert said intermediate N-protected prodrug ester to the corresponding naphthyridinone L-Ala-L-Ala prodrug acid final product [having formula (IV)], as indicated above, in the form of a pharmaceutically acceptable acid addition salt.

In this way, for example, a compound such as 7-[(1α,5α,6α)-6-(tert.-butoxycarbonylamino)-3-azabicyclo[3.1.0]hex-3-yl]-6-fluoro-1-(2,4-difluorophenyl)-1,4-dihydro-4-oxo-1,8-naphthyridine-3-carboxylic acid ethyl ester is readily converted, via the intermediates 7-[(1α,5α,6α)-6-amino-3-azabicyclo-[3.1.0]hex-3-yl]-6-fluoro-1-(2,4-difluorophenyl)-1,4-dihydro-4-oxo-1,8-naphthyridine-3-carboxylic acid ethyl ester and 7-[(1α,5α,6α)-6-(N-tert.-butoxycarbonyl-L-Ala-L-Ala-amino)-3-azabicyclo[3.1.0]hex-3-yl]-6-fluoro-1-(2,4-difluorophenyl)-1,4-dihydro-4-oxo-1,8-naphthyridine-3-carboxylic acid ethyl ester, to 7-[(1α,5α,6α)-6-(L-Ala-L-Ala-amino)-3-azabicyclo[3.1.0]hex-3-yl]-6-fluoro-1-(2,4-difluorophenyl)-1,4-dihydro-4-oxo-1,8-naphthyridine-3-carboxylic acid as a pharmaceutically acceptable acid addition salt and preferably, as the methanesulfonic acid addition salt. The latter prodrug acid final product is useful as a water-soluble prodrug of 7-[(1α,5α,6α)-6-amino-3-azabicyclo-[3.1.0]hex-3-yl]-6-fluoro-1-(2,4-difluorophenyl)-1,4-dihydro-4-oxo-1-naphthyridine-3-carboxylic acid, which is known to be useful as a therapeutically-effective antibacterial agent.

Accordingly, there is especially included within the purview of this invention a novel condensation method [step (b)] for preparing an N-protected prodrug ester compound of the formula:

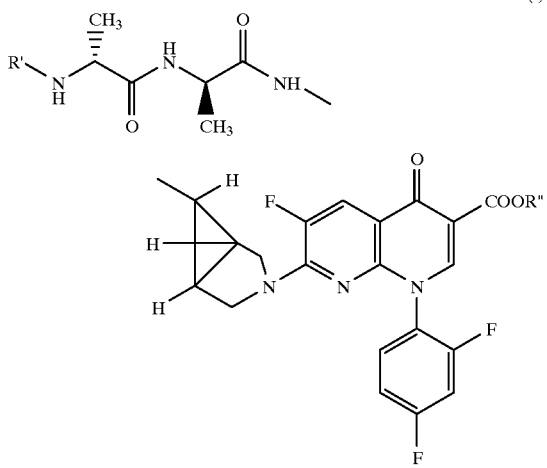

(I)

wherein R' is benzyloxycarbonyl, $C_1$–$C_4$ alkoxycarbonyl or $C_1$–$C_4$ alkanoyl and R" is an alkyl group having from one to four carbon atoms, which comprises the step of condensing the corresponding free amino ester compound of the formula

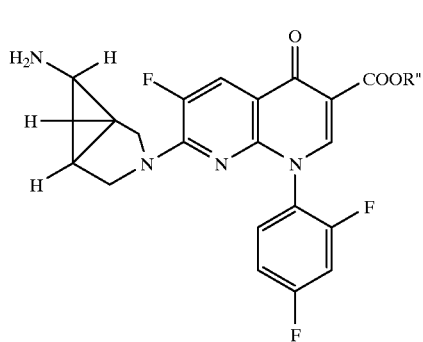

(II)

wherein R" is as previously defined, with at least an equimolar amount of a nitrogen-protected L-alanyl-L-alanine dipeptide compound of the formula

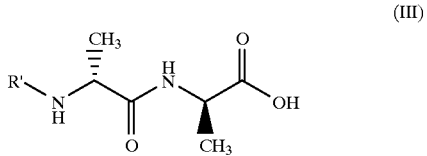

(III)

wherein R' is also as previously defined, in the presence of a standard organic dehydrating agent that is suitable for peptide bond formation, with the said condensation reaction being most efficiently conducted in a reaction-inert aprotic organic solvent at a temperature that is desirably in the range of from about 10° C. up to about 40° C., so as to yield the corresponding N-protected prodrug ester of the formula (I) as the desired condensation product of the reaction.

Additionally, the invention also especially includes within its scope a novel method of hydrolysis [step (c)] for preparing the corresponding prodrug acid, in the form of a pharmaceutically acceptable acid addition salt, from the corresponding N-protected prodrug ester compound of structural formula (I), obtained in the foregoing condensation reaction step, which further comprises subjecting the aforesaid N-protected prodrug ester compound to acid hydrolysis by contacting said ester with a mixture of water and a pharmaceutically-acceptable strong mineral or organic acid. More particularly, the hydrolysis reaction is most efficiently conducted in the presence of a water-miscible, reaction-inert polar organic as diluent and at a temperature that lies within the range of from about room temperature up to about the reflux temperature of the reaction mixture, so as to effectively cleave both the R' and R" groups from the structure (I) compound and thus afford the desired naphthyridinone antibacterial L-Ala-L-Ala prodrug acid compound having the formula

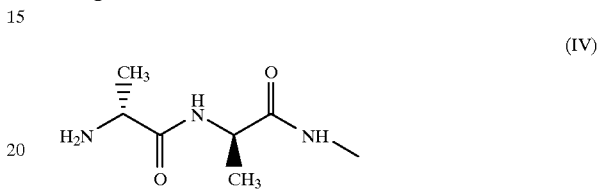

(IV)

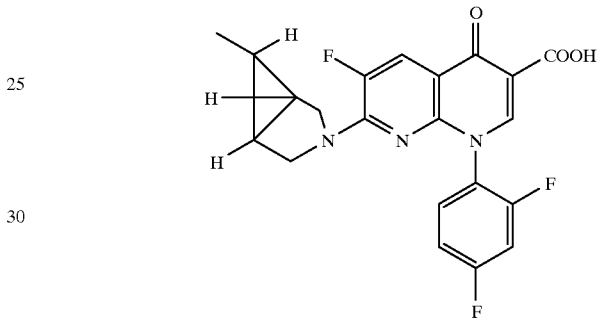

in the form of a pharmaceutically acceptable acid addition salt.

Also especially disclosed within the purview of this invention is a novel nitrogen-deprotecting method [step (a)] for preparing the step (c) free amino ester starting compound (i.e., N-deprotected drug ester) of structural formula (II), which involves treating a corresponding N-protected amino ester compound (i.e., N-protected drug ester) of the formula:

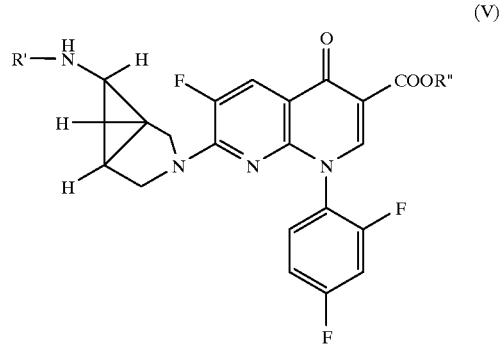

(V)

wherein R' is benzyloxycarbonyl, $C_1$–$C_4$ alkoxycarbonyl or $C_1$–$C_4$ alkanoyl and R" is an alkyl group having from one to four carbon atoms, with an excess in moles of a strongly-protic acid in the presence a reaction-inert aprotic organic solvent at a temperature that is most desirably in the range of from about 15° C. up to about 45° C., to selectively remove the $R^1$ group and so form the corresponding free amino ester compound of the aforesaid formula (II).

DISCLOSURE OF THE INVENTION

In accordance with the process of this invention, the initial stage (a) of the novel three-step reaction sequence for preparing the desired prodrug acid compound of formula (IV), in the form of a pharmaceutically acceptable acid addition salt, involves first removing the N-protecting group R' from the starting N-protected drug ester compound of structural formula (V) wherein $R^1$ is a $C_1$–$C_4$ alkanoyl group, or is a benzyloxycarbonyl group or is preferably a straight or branched-chain $C_1$–$C_4$ alkoxycarbonyl group and is most preferably, a tertiary-butoxycarbonyl group, and $R^{11}$ is an alkyl group having from one to four carbon atoms. This is most desirably accomplished by treating the appropriate 7-[(1α,5α,6α)-6-(alkanoyl or alkoxycarbonyl)amino-3-azabicyclo[3.1.0]-hex-3-yl]-6-fluoro-1-(2,4-difluorophenyl)-1,4 -dihydro-4-oxo-1,8-naphthyridine-3-carboxylic acid $C_1$–$C_4$ alkyl ester starting material (V) with an excess in moles of a strongly-protic acid in a reaction-inert aprotic organic solvent at a temperature that is in the range of from about 15° C. up to about 45° C., until the reaction to selectively remove the R' blocking group (while leaving the R" alkyl group intact) and so form the corresponding free amino ester compound of structural formula (II) is substantially complete. Preferred reaction-inert aprotic organic solvents for use in this connection include halogenated aromatic hydrocarbon solvents such as monochlorobenzene and dichlorobenzene, as well as various halogenated lower hydrocarbon solvents like methylene chloride, ethylene dichloride, chloroform, trichloroethylene, s-tetrachlorethane and carbon tetrachloride, etc. The most preferred solvents are o-dichlorobenzene and most especially, methylene chloride. Preferred strongly-protic acid reagents as catalysts for this particular reaction include, but are not limited to, sulfuric acid, methanesulfonic acid, trifluoromethanesulfonic acid, trifluoroacetic acid, polyphosphoric acid, as well as hydrohalide acids like hydrochloric acid and hydrobromic acid, with the most preferred member of the first four-named protic acids being trifluoroacetic acid (TFA). The molar ratio of the N-protected drug ester (V) starting material to the strongly-protic acid reagent employed as catalyst is not truly critical and so, a large excess in moles of the acid is generally employed in view of its ready availability. However, in practice, it is usually preferable to employ at about a ten molar excess of the acid with respect to the aforesaid N-protected drug ester starting material that is employed as substrate. In general, the selective N-deprotecting reaction is conducted at a temperature that is desirably in the range of from about 15° C. up to about 45° C., with the preferred temperature range for the reaction being between about 20° C. and about 30° C. Temperatures that are slightly above 45° C. are generally to be avoided, as care must be taken to ensure that the R" alkyl group of the alkoxycarbonyl moiety at the 3-position of the molecule is not effectively removed by hydrolytic cleavage under the conditions of the reaction. Under these terms, the reaction can be and, in practice, usually is run most effectively and efficiently at or near room or ambient temperatures (e.g., ca. 20° C.), for a period of at least about five hours (and preferably, about 5–24 hours) in order to ensure completeness of the selective N-protecting group removal. Upon completion of this step, the desired 7-[(1α,5α,6α)-6-amino-3-azabicyclo[3.1.0]hex-3-yl]-6-fluoro-1-(2,4-difluorophenyl)-1,4-dihydro-4-oxo-1,8-naphthyridine-3-carboxylic acid $C_1$–$C_4$ alkyl ester is readily recovered from the reaction mixture in a conventional manner common to these type reactions, viz., by concentration of the reaction mixture under reduced pressure, followed by basified dilution of the crude residual oil with aqueous base, such as a concentrated aqueous alkali metal hydroxide solution, e.g., 50% aqueous sodium hydroxide, and then further extraction of the basified aqueous mixture with the same organic solvent as was earlier employed in the N-deprotection reaction step per se, to ultimately yield the desired N-deprotected drug ester of structural formula (II) upon subsequent concentration of the organic extract thus obtained.

The second and next stage (b) of the three-step reaction process of this invention involves preparing the N-protected prodrug ester compound of structural formula (I) by condensing the corresponding N-deprotected drug ester (i.e., free amino ester) of structural formula (II), as obtained in step (a), with at least an equimolar amount of a nitrogen-protected L-alanyl-L-alanine dipeptide compound of structural formula (III), i.e., the so called N-protected-HN-L-Ala-L-Ala-COOH dipeptide, wherein R' in the formula is also as previously defined in the definition of structural formula (V). This particular condensation reaction is most desirably accomplished by reacting or condensing the appropriate 7-(1α,5α,6α)-6-amino-3-azabicyclo[3.1.0]hex-3-yl]-6-fluoro-1-(2,4-difluorophenyl)-1,4-dihydro-4-oxo-1,8-naphthyridine-3-carboxylic acid $C_1$–$C_4$alkyl ester (II) starting material, as already obtained in step (a), with the aforesaid N-protected L-alanyl-L-alanine dipeptide compound (III) in a reaction-inert aprotic organic solvent in the presence of a standard organic dehydrating agent, i.e., a coupling agent or promoter, that is normally suitable for peptide-bond formation. In the connection, it is to be noted that even though substantially equimolar amounts of N-deprotected drug ester reactant and N-protected L-alanyl-L-alanine (N-protected-HN-L-Ala-L-Ala-COOH) reagent are normally employed in carrying out the aforesaid condensation reaction, a slight excess of the more readily available N-protected-HN-L-Ala-L-Ala-COOH dipeptide reagent is usually preferred for the present purposes at hand. Preferred reaction-inert aprotic organic solvents for the condensation reaction at hand include aprotic polar organic solvents like tetrahydrofuran or dioxane, as well as aprotic non-polar organic solvents such as the halogenated aromatic hydrocarbons and halogenated lower hydrocarbons employed as solvents in the initial N-deprotecting step (a) of the overall three-step reaction process of the invention, with the most preferred halogenated hydrocarbon solvent again being methylene chloride. Suitable organic dehydrating or coupling agents (promoters) for the reaction include such reagents as N-ethoxycarbonyl-2-ethoxy-1,2-dihydroquinoline (EEDQ), as well as certain carbodiimide compounds like dicyclohexylcarbodiimide (DCC) and N,N-carbonyl-diimidazole; these agents are usually employed at molar levels that are substantially the same as the molar levels of the aforementioned 1,8-naphthyridine-3-carboxylic acid $C_1$–$C_4$ alkyl ester (II) starting material, with the corresponding ethyl ester being especially preferred as the starting material (reactant) of choice for the reaction. In general, the condensation reaction is most desirably conducted at a temperature that is in the range of from about 10° C. up to about 40° C. for a period of about two to about 16 hours, so as to yield the corresponding N-protected prodrug ester of the formula (I) as the desired condensation product of the reaction. Upon completion of this step, the desired 7-[(1α,5α,6α)-6-(N-protected-L-Ala-L-Ala-amino)-3-azabicyclo[3.1.0]-hex-3-yl]-6-fluoro-1-(2,4-difluorophenyl)-1,4-dihydro-4-oxo-1,8-naphthyridine-3-carboxylic acid $C_1$–$C_4$ alkyl ester is readily recovered from the reaction mixture in a conventional manner, viz., by first diluting and acidifying said mixture with aqueous hydrochloric acid, e.g., 0.1 N hydrochloric acid, and thereafter concentrating the acidified organic mixture to less than about one-quarter of the original volume, followed by the addition of a higher boiling solvent thereto in order to displace the first solvent via atmospheric distillation and so yield a suspension of the desired N-protected prodrug ester product of structural formula (I), which can then easily be isolated from the solvent mixture by means of filtration.

The third and final step (c) of the three-step reaction process of this invention involves hydrolyzing the N-protected prodrug ester of structural formula (I) to the corresponding prodrug acid final product of structural formula (IV) by contacting said prodrug ester with a mixture of water and a pharmaceutically-acceptable strong mineral or organic acid in the presence of a water-miscible but reaction-inert polar organic solvent as diluent at a temperature that is in the range of from about room temperature up to about the reflux temperature of the reaction mixture, so as to effectively cleave both the R' and R" groups from the structure (I) compound and thus afford the desired 1,8-naphthyridinone antibacterial L-Ala-L-Ala prodrug (IV) acid final product in the form of the corresponding pharmaceutically acceptable acid addition salt. Preferred water-miscible, reaction-inert polar organic solvents for use in this connection include such solvents as acetone, methyl ethyl ketone, dioxane, tetrahydrofuran and dimethyl sulfoxide, with the most preferred solvent being acetone. Preferred acids for use as catalytic-reagents in the hydrolysis reaction include pharmaceutically-acceptable strong mineral acids such as sulfuric acid, polyphosphoric acid, hydrochloric acid and hydrobromic acid, as well as pharmaceutically-acceptable strong organic acids like trifluoroacetic acid (TFA), methanesulfonic acid, benzenesulfonic acid and p-toluenesulfonic acid, with the most preferred member for the present purposes at hand being methanesulfonic acid. The amount of acid employed in the hydrolysis reaction at hand is not extremely critical, although it must necessarily be at least about equimolar with respect to the N-protected prodrug ester starting material of structural formula (I) in order to form the desired pharmaceutically acceptable acid addition salt. Nonetheless, in practice, it is usually preferable to employ an excess in moles of the acid (over the 1:1 ratio), and in this particular connection, an acid to N-protected prodrug ester (I) ratio of at least about 2:1, i.e., a ratio that is substantially at least about dimolar, is often considered most desirable in order to ensure completeness of the reaction. In general, the hydrolytic N-deprotecting reaction is conducted at a temperature that lies within the range of about room temperature (ca. 20° C.) up to about the reflux temperature of the reaction mixture, as aforesaid, with the preferred temperature range for the reaction being one that lies within the range of from about 40° C. up to about 65° C., especially when said reaction is carried out for a period of at least about 24 hours and preferably, for a period of about one to about four days. Upon completion of this step, the desired prodrug acid of structural formula (IV), viz., 7-[(1α,5α,6α)-6-(L-Ala-L-Ala-amino)-3-azabicyclo[3.1.0] hex-3-yl]-6-fluoro-1-(2,4-difluorophenyl)-1,4-dihydro-4oxo-1-napthyridine-3-carboxylic acid is readily recovered from the reaction mixture in the form of a pharmaceutically acceptable acid addition salt by conventional means, e.g., by first cooling the resulting aqueous organic reaction system to ambient temperatures and then isolating the solid product from the thus-formed suspension by means of suction filtration and the like, followed by vacuum drying to constant weight, etc. In this way, the novel three-step reaction process for preparing the desired water-soluble prodrug acid final product of structural formula (IV), in the form of a pharmaceutically acceptable acid addition salt, such as, for example, the methanesulfonic acid addition salt of 7-[(1α,5α,6α)-6-(L-Ala-L-Ala-amino)-3-azabicyclo[3.1.0]hex-3-yl]-6-fluoro-1-(2,4-difluorophenyl)-1,4-dihydro-4-oxo-1-naphthyridine-3-carboxylic acid, i.e., the methanesulfonate or mesylate salt, starting from the corresponding N-protected drug ester of structural formula (V), is now complete.

The 7-[(1α,5α,6α)-6-(alkanoyl and alkoxycarbonyl) amino-3-azabicyclo[3.1.0]hex-3-yl]-6-fluoro-1-(2,4-difluorophenyl)-1,4-dihydro-4-oxo-1,8-naphthyridine-3-carboxylic acid $C_1$–$C_4$ alkyl esters (i.e., N-protected drug esters) of structural formula (V), required as the ultimate starting materials for conducting the novel three-step reaction process of this invention, are known compounds which can easily be synthesized by those skilled in the art, starting from readily available materials and employing the reaction procedures already described by K. E. Brighty in U.S. Pat. No. 5,164,402 (1992).

The prodrug acid compound of structural formula (IV) and its non-toxic salts that are produced by the process of the present invention, viz., 7-[(1α,5α,6α)-6-(L-Ala-L-Ala-amino)-3-aza-[3.1.0]hex-3-yl]-6-fluoro-1-(2,4-difluorophenyl)-1,4-dihydro-4-oxo-1,8-naphthyridine-3-carboxylic acid and its pharmaceutically acceptable acid addition salts, are all known to be useful in therapy as antibacterial agents for treating various bacterial infections of the broad spectrum type and particularly, for treating bacterial infections of Gram-positive strains. Appropriate dosage ranges and methods of administration for the prodrug acid (IV) and its pharmaceutically acceptable salts are already adequately set forth in aforementioned U.S. Pat. No. 5,164,402 to K. E. Brighty, along with a method by which the antibacterial activity of such a prodrug acid and its aforesaid non-toxic salts can be readily determined.

Hence, the novel process of the present invention now provides the required and valuable water-soluble prodrug acid (IV) companion to the corresponding drug acid discussed above, in the form of a pharmaceutically acceptable acid addition salt, in pure solid form and in high yield, by a unique three-step overall method of synthesis. The later accomplishment, in turn, represents a major improvement over the prior art methods previously disclosed in aforesaid U.S. Pat. No. 5,164,402 to K. E. Brighty, especially in view of the ease of synthesis and the greatly reduced nature of the costs involved in the overall method of production. More specifically, the three-step overall yield averages more than 60%, based on the known and previously-discussed starting N-protected amino ester (V) and proceeding through the corresponding N-deprotected amino ester (II) and N-protected prodrug ester (I) intermediates to eventually yield the desired prodrug acid (IV) final product in the form of a pharmaceutically acceptable acid, as aforesaid. Moreover, both intermediates are easily isolated by means of conventional crystallization techniques and there is no scrambling of the dipeptide stereochemistry in proceeding from (I) to (IV) during the final hydrolysis step.

PREPARATION A

A well-stirred solution consisting of 300 g (0.783 mole) of the ethyl ester of 7-chloro-6-fluoro-1-(2,4-difluorophenyl)-1,4-dihydro-4-oxo-1,8-naphthyridine-3-carboxylic acid (see U.S. Pat. Nos. 4,571,396 and 4,775,668), 146 g (0.737 mole) of 1α,5α,6α-6-(tert.-butoxycarbonylamino)-3-azabicyclo

[3.1.0]-hexane (prepared as described by K. E. Brighty in U.S. Pat. No. 5,164,402 and 470 ml (3.386 mole) of triethylamine dissolved in 3.0 liters of methylene chloride was heated to the reflux temperature (ca. 40° C.) and thereafter maintained at that point for a period of approximately 16 hours (i.e., overnight). During this time period, a white solid was observed to precipitate from the reaction solution. After cooling the entire system to room temperature (ca. 20° C.), 7.5 liters of methylene chloride and 6.0 liters of water were added to the cooled solution at ambient temperature. The two resultant layers so obtained were then separated, and the organic layer was thereafter filtered to remove a small amount of an insoluble solid material. The organic solution obtained as filtrate was then concentrated via atmospheric distillation to 2.5 liters, at which point a white precipitate was observed to form. The resulting suspension was next diluted to a total volume of 5.0 liters by means of added ethyl acetate, and atmospheric distillation was then resumed until the concentrate eventually reached a total volume of 3.0 liters (this was done to displace methylene chloride). The final suspension was subsequently cooled to ambient temperature and thereafter granulated at that point for a period of two hours. Isolation of the desired product was then achieved by means of suction filtration, followed by drying in vacuo to constant weight to ultimately afford 406.7 g (95%) of pure 7-[(1α,5α,6α)-6-(tert.-butoxycarbonylamino)-3-azabicyclo[3.1.0]hexyl-3-yl]-6-fluoro-1-(2,4-difluorophenyl)-1,4-dihydro-4-oxo-1,8-naphthyridine-3-carboxylic acid ethyl ester. The pure product was found to be substantially identical with that of an authentic sample of the known compound as first prepared and reported (by K. E. Brighty in U.S. Pat. No. 5,164,402), as attested to by both high pressure liquid chromatography (HPLC) analysis and proton nuclear magnetic resonance ($^1$HNMR) data.

EXAMPLE 1

A solution consisting of 395 g (0.725 mole) of 7-[(1α,5α,6α)-6-tert.-butoxycarbonylamino)-3-azabicyclo[3.1.0]hex-3-yl]-6-fluoro-1-(2,4-difluorophenyl)-1,4-dihydro-4-oxo-1,8-napththyridine carboxylic acid ethyl ester (the product of Preparation A) dissolved in 4.0 liters of methylene chloride was stirred at room temperature (ca. 20° C.), while 725 ml (9.412 mole) of trifluoroacetic acid slowly added thereto over a period of ten minutes. The resulting reaction mixture was next stirred at ambient temperature for a period of 17 hours, followed by concentration in vacuo to eventually yield a crude residual oil. This oil was then diluted with 5.0 liters of water and basified with 50% aqueous sodium hydroxide solution, followed by successive extractions with 6-liter and liter portions of methylene chloride in that order. The two organic extracts were next combined and subsequently filtered to remove a small amount of an insoluble solid material, followed by concentration of the resulting filtrate to yield a semi-solid residue. Trituration of the latter material with 4.0 liters of ethyl acetate, followed by a subsequent reduction in volume to 2.0 liters via atmospheric distillation (to displace methylene chloride) then gave a final organic suspension that was thereafter granulated at 10° C. for a period of one hour. Isolation of the desired product was next accomplished by means of suction filtration, followed by drying of the product in vacuo to constant weight to ultimately afford 284 g (88%) of pure 7-[(1α,5α,6α)-6-amino-3-azabicyclo[3.1.0]hex-3-yl]-6-fluoro-1-(2,4-difluorophenyl)-1,4-dihydro-4-oxo-1,8-naphthyridin-3-carboxylic acid ethyl ester, m.p. 208–210° C. The pure product was further characterized by means of high pressure liquid chromatography (HPLC) analysis and proton nuclear magnetic resonance ($^1$HNMR) data and the respective spectra were both found to be consistent for the desired product.

EXAMPLE 2

To a well-stirred mixture consisting of 270 g (0.678 mole) of 7-[(1α,5α,6α)-6-amino-3-azabicyclo[3.1.0]hex-3-yl]-6-fluoro-1-(2,4-difluorophenyl)-1,4-dihydro-4-oxo-1,8-naphthyridine-3-carboxylic acid ethyl ester (the product of Example 1) and 185 g (0.717 mole) of N-tert.-butoxycarbonyl-L-alanyl-L-alanine (t-BOC-HN-L-Ala-L-Ala-COOH dipeptide) suspended in 4.0 liter of methylene chloride, there were added 165 g (0.665 mole) of 1-ethoxy-2-ethoxycarbonyl-1,2-dihydroquinoline (EEDQ) at room temperature (ca. 20° C.). Upon completion of this step, resulting reaction solution was stirred at ambient temperature for a period of four hours and then diluted with 4.0 liters of 1 N hydrochloric acid. The product-rich organic layer was next separated from the aqueous phase and the saved organic phase was thereafter concentrated to a volume of 500 ml via atmospheric distillation. At this point, 1.5 liters of acetonitrile were added to the concentrate, followed by further distillation of the mixture at atmospheric pressure until a total volume of 500 ml of concentrate was again achieved (this was done to displace methylene chloride). The final suspension was then cooled to ambient temperature with stirring, and the granulated mixture so obtained was subsequently subjected to suction filtration in order to recover the desired solid product from the mixture. After drying the thus isolated product in vacuo to constant weight, there were ultimately obtained 368 g (92%) of pure 7-[(1α,5α,6α)-6-(N-tert.-butoxycarbonyl-L-Ala-L-Ala-amino)-3-aza-bicyclo[3.1.0]hex-3-yl]-6-fluoro-1-(2,4-difluorophenyl)-1,4-dihydro-4-oxo-1,8-naphthyridine-3-carboxylic acid ethyl ester, m.p. 218–220° C. The pure product was further characterized by means of high pressure liquid chromatography (HPLC) analysis and proton nuclear magnetic resonance ($^1$HNMR) data, and the respective spectra were both found to be consistent for the desired compound.

EXAMPLE 3

A well-stirred solution consisting of 350 g (0.510 mole) 7-[(1α,5α,6α)-6-(N-tert.-butoxycarbonyl-L-Ala-L-Ala-amino)-3-azabicyclo[3.1.0]hex-3-yl]-6-fluoro-1-(2,4-difluorophenyl)-1,4-dihydro-4-oxo-1,8-naphthyridine-3-carboxylic acid ethyl ester (the product of Example 2) dissolved in 5.25 liters of acetone and 40 ml of water was treated with 77 ml (1.187 mole) of methanesulfonic acid at room temperature (ca. 20° C.) and then filtered under spec-free conditions. The resulting reaction solution obtained as the filtrate was next heated to reflux and thereafter maintained at that point for a period of 72 hours. During course of the reflux heating period, 25 ml of water and 5 ml of methanesulfonic acid were additionally added. Upon completion of the entire reaction step, a white suspension had formed and the resulting aqueous organic system was subsequently cooled to ambient temperature. Isolation of the desired product was then accomplished by means of suction filtration, followed by drying of the filtered product in vacuo to constant weight to ultimately afford 246 g (70%) of pure 7-[(1α,5α,6α)-6-(L-Ala-L-Ala-amino)-3-azabicyclo[3.1.0]hex-3-yl]-6-fluoro-1-(2,4-difluorophenyl)-1,4-dihydro-4-oxo-1,8-naphthyridine carboxylic acid, as the methanesulfonate (i.e., mesylate) salt, m.p. 205–206° C.; $[\alpha]_D^{25°}$ –39.7° (c=0.47, methanol). The pure product was further characterized by means of high pressure liquid chromatography (HPLC) analysis and proton nuclear magnetic resonance ($^1$HNMR) data, and the respective spectra were both found to be consistent for the desired product.

In order to render the final product pyrogen-free for pharmaceutical use in humans, 235 g of the pure final product obtained as above was suspended in pyrogen-free acetone, using pyrogen-free equipment and with constant agitation being maintained throughout this step. The resulting suspension was then subjected to suction filtration and the recovered solid product subsequently dried in vacuo to constant weight to ultimately give 220 g of pyrogen-free, pure 7-[(1α,5α,6α)-6-(L-Ala-L-Ala-amino)-3-azabicyclo[3.1.0]hexy-3-yl]-6-fluoro-1-(2,4-difluorophenyl)-1,4-dihydro-4-oxo-1,8-naphthyridine-3-carboxylic acid, as the methanesulfonic acid (mesylate) salt, in the form of a fine material of proven finished goods quality.

We claim:

1. A process for preparing a pharmaceutically acceptable acid addition salt of a prodrug acid of a naphthyridinone antibiotic compound having the formula:

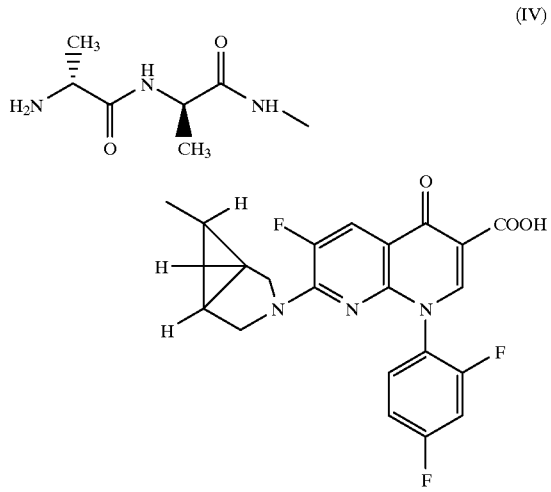

(IV)

which comprises the steps of
(a) treating a corresponding ester compound of the formula

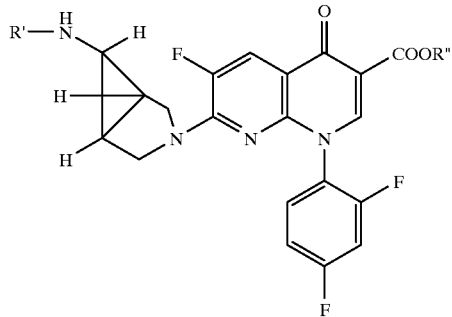

(V)

wherein R' is benzyloxycarbonyl, $C_1$–$C_4$ alkoxycarbonyl or $C_1$–$C_4$ alkanoyl and R" is an alkyl group having from one to four carbon atoms, with an excess in moles of a strongly protic acid in a reaction-inert aprotic organic solvent, to selectively remove the R' group and so form the corresponding free amino ester compound of the formula

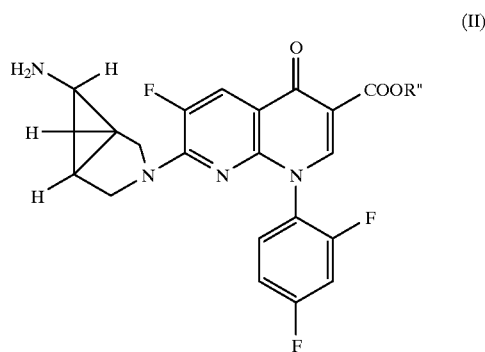

(II)

wherein R" still remains as previously defined;
(b) condensing the intermediate free amino ester compound of structural formula (II), obtained as above in step (a), with at least an equimolar amount of a nitrogen-protected L-Ala-L-Ala dipeptide compound of the formula

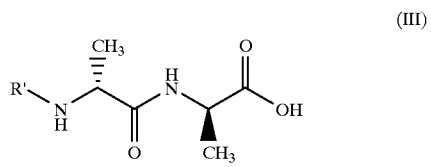

(III)

wherein R' is as previously defined, in the presence of a standard organic dehydrating agent that is suitable for peptide bond formation, with said overall condensation reaction being conducted in a reaction-inert aprotic organic solvent, to yield the corresponding N-protected prodrug ester of the formula

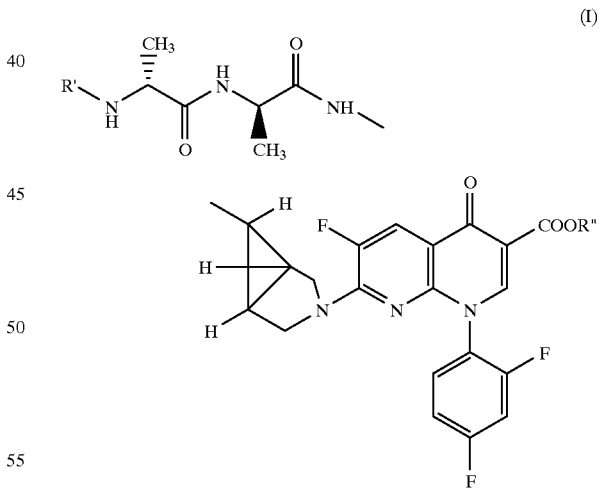

(I)

wherein R' and R" are again each as previously defined, as the desired condensation product of the reaction; and
(c) thereafter subjecting the N-protected prodrug ester compound of structural formula (I), obtained as above in step (b), to acid hydrolysis by contacting said ester with a mixture of water and a pharmaceutically-acceptable strong mineral or organic acid, with said hydrolysis reaction being conducted in the presence of a water-miscible but reaction-inert polar organic solvent as diluent to effectively cleave both the R' and R"

groups from the structure (I) compound and thus afford the desired naphthyridinone antibiotic L-Ala-L-Ala prodrug acid of structural formula (IV) in the form of the corresponding pharmaceutically acceptable acid addition salt.

2. A process for preparing an N-protected prodrug ester compound of the formula:

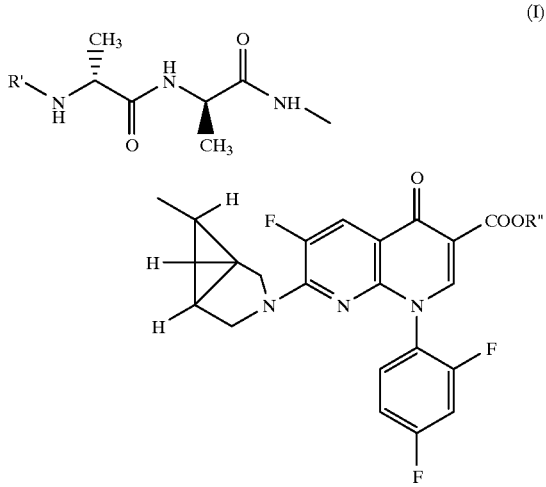

wherein R' is benzyloxycarbonyl, $C_1$–$C_4$ alkoxycarbonyl or $C_1$–$C_4$ alkanoyl and R" is an alkyl group having from one to four carbon atoms, which comprises the step of condensing the corresponding free amino ester compound of the formula

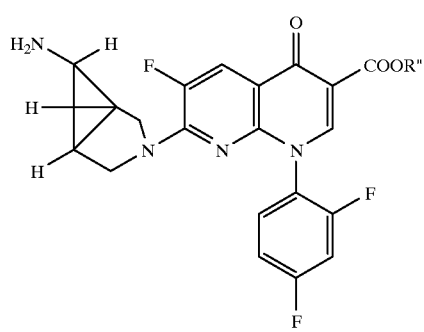

wherein R" is as previously defined, with at least an equimolar amount of a nitrogen-protected L-alanyl-L-alanine dipeptide compound of the formula

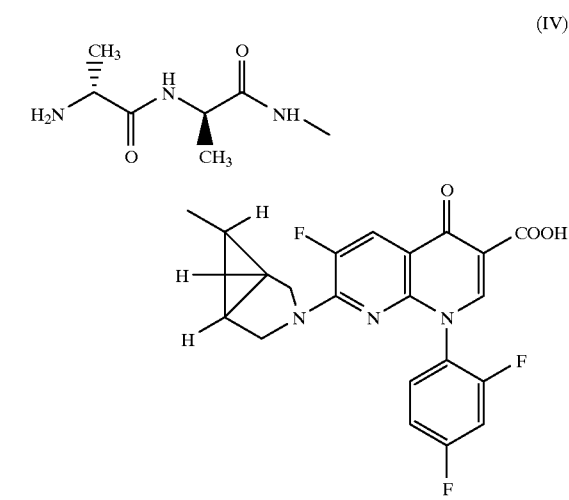

wherein R' is also as previously defined, in the presence of a standard organic dehydrating agent that is suitable for peptide bond formation, with said condensation reaction step being conducted in a reaction-inert aprotic organic solvent at a temperature that is in the range of from about 10° C. up to about 40° C., so as to yield the corresponding N-protected prodrug ester of the formula (I) as the desired condensation product of the reaction.

3. A process as claimed in claim 2 wherein R' is a tert.-butoxycarbonyl group and R" is an ethyl group.

4. A process as claimed in claim 2 wherein the reaction-inert aprotic organic solvent employed in the condensation reaction step is a chlorinated lower hydrocarbon solvent.

5. A process as claimed in claim 4 wherein the chlorinated lower hydrocarbon solvent is methylene chloride.

6. A process as claimed in claim 2 wherein the dehydrating agent employed in the condensation reaction step is dicyclohexyl-carbodiimide or 1-ethoxy-2-ethoxycarbonyl-1,2-dihydroquinoline.

7. A process as claimed in claim 6 wherein the dehydrating agent employed is 1-ethoxy-2-ethoxycarbonyl-1,2-dihydroquinoline.

8. A process as claimed in claim 2 wherein the amount of dehydrating agent employed in the condensation reaction step is substantially equmolar with respect to the free amino ester intermediate starting compound of structural formula (II).

9. A process as claimed in claim 2, which further comprises subjecting the N-protected prodrug ester compound of structural formula (I), obtained in the condensation reaction step of said process, to acid hydrolysis by contacting said ester with a mixture of water and a pharmaceutically-acceptable strong mineral or organic acid, with said hydrolysis reaction being conducted in the presence of a water-miscible, reaction-inert polar organic solvent as diluent and at a temperature that lies within the range of from about room temperature up to about the reflux temperature of the reaction mixture, so as to effectively cleave both the R' and R" groups from the structure (I) compound and thus afford the desired naphthyryridinone antibacterial L-Ala-L-Ala prodrug having the formula:

(IV)

in the form of a pharmaceutically acceptable acid addition salt.

10. A process as claimed in claim 9 wherein the water-miscible polar organic solvent employed in the acid hydrolysis reaction step is selected from acetone, methyl ethyl ketone, dioxane, tetrahydrofuran or dimethylsulfoxide.

11. A process as claimed in claim 10 wherein the solvent employed is acetone.

12. A process as claimed in claim 9 wherein the acid employed in the acid hydrolysis reaction step is selected from hydrochloric acid, methanesulfonic acid or p-toluenesulfonic acid.

13. A process as claimed in claim 12 wherein the acid employed is methanesulfonic acid.

14. A process as claimed in claim 9 wherein the amount of acid employed in the acid hydrolysis reaction step is substantially at least about dimolar with respect to the N-protected prodrug ester intermediate starting compound of structural formula (I).

15. A process as claimed in claim 9 wherein the acid hydrolysis reaction step is conducted at a temperature that lies within the range of from about 40° C. up to 65° C.

16. A process as claimed in claim 11 wherein the acid employed in the acid hydrolysis step is methanesulfonic acid and the final product is recovered from the reaction mixture in the form of the methanesulfonate acid addition salt.

17. A process as claimed in claim 2, wherein the corresponding free amino ester starting compound of structural formula (II) is prepared by treating a corresponding N-protected amino ester compound of the formula

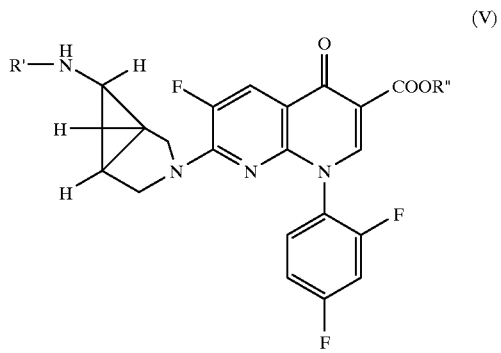

(V)

wherein R' is benzyloxycarbonyl, $C_1$–$C_4$ alkoxycarbonyl or $C_1$–$C_4$ alkanoyl and R" is an alkyl group having from one to four carbon atoms, with an excess in moles of a strongly-protic acid in a reaction-inert aprotic organic solvent at a temperature that is in the range of from about 15° C. up to about 45° C. to selectively remove the R' group and so form the corresponding free amino ester compound of the formula (II).

18. A process as claimed in claim 17 wherein $R^1$ is a tert-butoxycarbonyl group.

19. A process as claimed in claim 17 wherein the strongly-protic acid employed is trifluoroacetic acid.

20. A process as claimed in claim 17 wherein the reaction-inert aprotic organic solvent employed is a chlorinated lower hydrocarbon solvent.

21. A process as claimed in claim 20 wherein the chlorinated lower hydrocarbon solvent is methylene chloride.

* * * * *